United States Patent [19]

Nagel

[11] Patent Number: 5,153,206

[45] Date of Patent: Oct. 6, 1992

[54] ARYLPIPERIDINE DERIVATIVES

[75] Inventor: Arthur A. Nagel, Gales Ferry, Conn.

[73] Assignee: Pfizer Inc., New York, N.Y.

[21] Appl. No.: 566,435

[22] PCT Filed: Dec. 2, 1988

[86] PCT No.: PCT/US88/04300

§ 371 Date: Jul. 26, 1990

§ 102(e) Date: Jul. 26, 1990

[87] PCT Pub. No.: WO90/06303

PCT Pub. Date: Jun. 14, 1990

[51] Int. Cl.$^5$ .................. A61K 31/445; A01N 43/40; C07D 211/40

[52] U.S. Cl. ..................... 514/326; 546/209; 546/192; 546/201; 546/282; 546/16; 546/183; 514/278; 514/258; 514/299; 514/317; 514/323; 544/282

[58] Field of Search ............ 546/209; 514/326

[56] References Cited

U.S. PATENT DOCUMENTS

| | | | |
|---|---|---|---|
| 2,604,473 | 7/1950 | Sperber et al. | 546/209 |
| 3,717,634 | 2/1973 | Wu et al. | 260/256.4 |
| 4,458,076 | 7/1984 | Strupczewski | 546/199 |
| 4,777,178 | 10/1988 | Nakai et al. | 514/326 |
| 4,831,031 | 5/1989 | Lowe, III et al. | 514/254 |
| 4,891,375 | 1/1990 | Lowe, III | 514/252 |
| 5,086,054 | 2/1992 | Parish | 514/239.2 |
| 5,086,063 | 2/1992 | Ciganek et al. | 514/326 |

FOREIGN PATENT DOCUMENTS 0196132 10/1986 European Pat. Off. .
281309 9/1988 European Pat. Off. .

OTHER PUBLICATIONS

"Dopamine Receptor Binding Predicts Clinical and Pharmacological Potencies of Antischizophrenic Drugs," by Ian Creese et al., Science, vol. 190, p. 481 (1976).

Primary Examiner—Mukund J. Shah
Assistant Examiner—Matthew V. Grumbling
Attorney, Agent, or Firm—Peter C. Richardson; Paul H. Ginsburg

[57] ABSTRACT

A series of novel N-alkyl or oxyalkyl arylpiperidine derivatives have been prepared, including their pharmaceutically acceptable acid addition salts, wherein the N-alkyl or oxyalkyl side chain is further substituted by certain aryl or heterocyclic ring groups. These particular compounds are useful in therapy as neuroleptic agents for the control of various psychotic disorders. Typical and preferred member compounds include 4-{{4-{2-[4-(2-methoxyphenyl)-1-piperidinyl]ethyl}phenyl}}thiazole-2-amine, 4-{{4-{4-[4-(2-methoxyphenyl)-1-piperidinyl]-n-butyl}phenyl}}thiazole-2-amine, 3-{4-[4-(2-methoxyphenyl)-1-piperidinyl]-n-butyl}-1,8,8-trimethyl-3-azabicyclo[3.2.1]octane-2,4-dione, 5-{2-[4-(2-methoxyphenyl)-1-piperidinyl]ethyl}oxindole and 3-{2-[4-(1-naphthyl)-1-piperidinyl]ethyl}-2-methyl-4H-pyrido[1,2-a]pyrimidine-4-one, respectively. Methods for preparing all these compounds from known starting materials are provided.

14 Claims, No Drawings

ARYLPIPERIDINE DERIVATIVES

TECHNICAL FIELD

This invention relates to new and useful arylpiperidine derivatives of interest to those in the field of medicinal chemistry and chemotherapy. More particularly, it is concerned with a novel series of N-alkyl or oxyalkyl arylpiperidine compounds, including their pharmaceutically acceptable acid addition salts, that are further substituted on the alkyl or oxyalkyl side chain by certain aryl or heterocyclic ring groups. These particular compounds are useful in therapy as neuroleptic agents for the control of various psychotic disorders.

BACKGROUND ART

In the past, various attempts have been made to obtain new and better anti-psychotic agents. These efforts have involved the synthesis and testing of various N-alkyl-N-arylpiperazine derivatives that are further substituted on the alkyl side chain by various aryl or heterocyclic ring groups. For instance, in U.S. Pat. Nos. 2,927,924 and 3,170,926, there are disclosed various N-phenylethyl-N'-arylpiperazine compounds that are reported to be useful for these purposes, while in U.S. Pat. No. 4,558,060 and in Published European Patent Application Nos. 279,598 (published on Aug. 24, 1988) and 281,309 (published on Sept. 7, 1988), there are disclosed the corresponding N-heterocyclylalkyl-N'-arylpiperazine compounds. Other efforts have involved the synthesis and testing of various arylpiperidine derivatives in this area, for example, U.S. Pat. No. 4,458,076 and Published European Patent Application No. 196,132 both teach a series of N-substituted 1,2-benzoisothiazol-3-ylpiperidine derivatives, which are also reported to be useful as anti-psychotic agents. However, none of the foregoing references teach or suggest the heretofore unavailable N-alkyl arylpiperidine derivatives or their use for anti-psychotic purposes.

DISCLOSURE OF THE INVENTION

In accordance with the present invention, it has now been found that certain novel N-alkyl or oxyalkyl derivatives of various arylpiperidine compounds are useful in therapy as neuroleptic agents for the control of various psychotic disorders. More specifically, the novel compounds of this invention are N-substituted arylpiperidines of the formula:

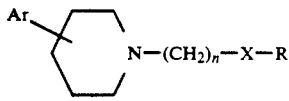
I and the pharmaceutically acceptable acid addition salts thereof, wherein Ar is phenyl, fluorophenyl, chlorophenyl, trifluoromethylphenyl, methoxyphenyl, tolyl or naphthyl optionally substituted with fluorine, chlorine, trifluoromethyl or methoxy; n is an integer of from two to four, inclusive; X is oxygen, sulfur or a direct link; and R is phenyl, hydroxyphenyl, methoxyphenyl, tolyl, 2-amino-4-thiazolylphenyl, 5-oxindolyl, 2-methyl-4-oxo-4H-pyrido[1,2a]pyrimidin-3-yl, 7,9-dioxo-8-azaspiro[4.5]decan-8-yl or 1,8,8-trimethyl-2,4-dioxo-3-azabicyclo-[3.2.1]octan-3-yl. These novel compounds are dopamine-2 antagonists and additionally possess the ability to reverse haldol-induced catalepsy in animals, so that they are useful in treating various psychotic disorders in mammals without causing any untoward side effects.

A preferred group of compounds of the present invention of particular interest is that of the aforesaid formula I wherein Ar is phenyl, trifluoromethylphenyl, methoxyphenyl or naphthyl, X is oxygen or a direct link and R is phenyl, hydroxyphenyl, 2-amino-4-thiazolylphenyl, 5-oxindolyl, 2-methyl-4-oxo-4H-pyrido[1,2a]pyrimidin-3yl, 7,9-dioxo-8-azaspiro[4.5]decan-8-yl or 1,8,8-trimethyl-2,4-dioxo-3-azabicyclo[3.2.1]octan-3-yl. Especially preferred compounds within this group include those members where Ar is 2-methoxyphenyl or 1-naphthyl, X is a direct link and R is 2-amino-4-thiazolylphenyl, 5-oxindolyl, 2-methyl-4-oxo-4H-pyrido[1,2-a]pyrimidin-3-yl or 1,8,8-triethyl-2,4-dioxo-3-azabicyclo]3.2.1]-octan-3yl.

Of especial interest in this connection are such typical and preferred compounds of the invention as 4-{{4-{2-[4-(2-methoxyphenyl)-1-piperidinyl]ethyl}-phenyl{{ thiazole-2-amine, 4-{{4-{4-[4-(2-methoxyphenyl)-1-piperidinyl]-n-butyl}phenyl}}thiazole-2-amine, 3-{4-[4-(2-methoxyphenyl)-1-piperidinyl]-n-butyl}-1,8,8-trimethyl-3-azabicyclo-[3.2.1]octane-2,4-dione, 5-{2-[4-(2-methoxyphenyl)-1-piperidinyl]ethyl}oxindole and 3-{2-[4-(1-naphthyl)-1-piperidinyl]ethyl}-2-methyl-4H-pyrido[1,2-a]pyrimidine-4-one, respectively, There is also included within the purview of this invention various novel pharmaceutical compositions useful for treating psychotic disorders in a mammal in need of such treatment, comprising a pharmaceutically acceptable carrier or diluent and a therapeutically-effective amount of a compound of the formula I, or a pharmaceutically acceptable acid addition salt thereof, wherein Ar, n, X and R are each as previously defined.

DETAILED DESCRIPTION

In accordance with the process employed for preparing the novel compounds of this invention, an arylpiperidine compound of the formula:

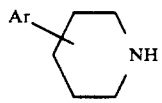
II wherein Ar is defined as aforesaid, is treated with at least an equivalent amount in moles of an aralkyl (or aryloxyalkyl) or heterocyclylalkyl ether derivative or a corresponding halide of the formula:

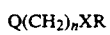

wherein R, X and n are each as previously defined and Q is a "leaving group" such as p-toluenesulfonyloxy (p-tosyloxy) or a halogen like chlorine or bromine. This reaction is normally carried out in a reaction-inert polar organic solvent, preferably under substantially anhydrous conditions, in the presence of at least an equivalent amount of an appropriate standard base to neutralize the acid byproduct. Preferred reaction-inert polar organic solvents for use in this connection include cyclic ethers such as dioxane and tetrahydrofuran, lower alkanols ($C_1$-$C_5$) such as methanol, ethanol, isopropanol, n-butanol and isoamyl alcohol, lower alkyl ketones such as acetone, methyl ethyl ketone, methyl isobutyl ketone and the like, lower dialkyl sulfoxides such as dimethyl and diethylsulfoxide, etc., and even N,N-dialkyl lower alkanoamides such as N,N-dimethylformamide, N,N-dimethylacetamide, N,N-diethylformamide and the like. A particularly convenient reaction system employs acetone or methyl isobutyl ketone as the solvent and potassium or sodium carbonate as the base, with up to three or more equivalents of sodium iodide added, if desired, to enhance the rate of the reaction. It should be noted that the amount of standard base employed must be such that it is always present in sufficient amount to neutralize the liberated acid byproduct formed in the reaction, as previously discussed. Excess of the reagent $RX(CH_2)_nQ$ is usually not critical to the reaction, but such excess will generally be used in order to shift the reaction equilibrium to completion in a shorter period of time. In this connection, it should also be borne in mind that the rate of reaction will also depend to some extent on the nature of Q (e.g., Cl>Br). In general, the reaction is conducted at a temperature of from about 50° C. up to about 150° C. for a period of about two to about 24 hours. The reaction pressure is not critical, e.g., a reaction pressure of about 0.5 to about 2.0 atmospheres is generally employed, with the preferred pressure usually being at or near ambient pressure (i.e., at about one atmosphere). When acetone or methyl isobutyl ketone is employed as the solvent and potassium or sodium carbonate as the base, the reflux temperature of the reaction mixture is a particularly convenient reaction temperature for these purposes. The reaction is also conveniently followed by thin layer chromatography, thereby determining reaction times sufficient to provide complete reaction and at the same time avoiding any unnecessary heating and excessive reaction times which can increase the level of unwanted byproduct formation and reduce yields. Upon completion of the reaction, the desired N-alkyl or oxyalkyl arylpiperidine final product is then conveniently isolated from the reaction mixture and purified in a conventional manner. It should be noted in this connection that the ether derivatives or halides $[Q(CH_2)_nXR]$ employed as reagent in this reaction are, for the most part, known compounds or else they can easily be prepared by those skilled in the art from readily available starting materials, using the standard synthetic procedures of organic chemistry (e.g., see Preparations P–S in this regard).

The arylpiperidine starting materials (i.e., the organic amine base compounds of structural formula II) required for preparing the desired final products of structural formula I in the herein described process of this invention are also, for the most part, new compounds, which are most conveniently prepared by a multi-step series of reactions starting from readily available organic materials. For example, the N-unsubstituted arylpiperidine compounds of the formula II are prepared in an elegant fashion (in three steps) from the known aryl bromides by (1) reacting the latter with magnesium in a Grignard reaction to form the corresponding Grignard reagent (ArMgBr) and thereafter immediately treating said reagent with 1-benzyl-3-piperidone or 1-benzyl-4-piperidone to ultimately form the corresponding 1-benzyl-3-hydroxy-3-aryl- or 1-benzyl-4-hydroxy-4-arylpiperidines (e.g., see Preparations A–D in this regard); followed by (2) dehydration of the latter type compounds to the corresponding 1-benzyl-3,4-dehydro-3(4)-arylpiperidines via treatment with triethylsilane in chilled trifluoroacetic acid (e.g., see Preparations F–J in this regard); and thereafter (3) finally converting said 3,4-dehydro compounds to the desired arylpiperidines by means of hydrogenolysis using catalytic hydrogenation in an acid medium (e.g., see Preparations K–O in this regard). In this way, 1-bromonaphthalene is readily converted, via 1-benzyl-4-hydroxy-4-(1-naphthyl)-piperidine and 1-benzyl-3,4-dehydro-4-(1-naphthyl)-piperidine, to 4-(1-naphthyl)piperidine.

Inasmuch as the N-substituted arylpiperidine compounds of this invention are basic compounds, they form salts with various inorganic and organic acids. Although such salts must be pharmaceutically acceptable for administration to animals, it is often desirable in practice to initially isolate the N-substituted arylpiperidine base compound from the reaction mixture as a pharmaceutically unacceptable salt and then simply convert the latter back to the free base compound by treatment with an alkaline reagent and thereafter, subsequently convert the latter free base to a pharmaceutically acceptable acid addition salt. The acid addition salts of the N-substituted arylpiperidine base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The acids which are used to prepare the pharmaceutically acceptable acid addition salts of the aforementioned N-substituted arylpiperidine base compounds of this invention are those which form non-toxic acid addition salts, i.e., salts containing pharmacologically acceptable anions, such as the hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis(2-hydroxy-3-naphthoate)] salts.

The novel N-substituted arylpiperidine compounds of the present invention are all readily adapted to therapeutic use as neuroleptic agents for the control of various psychotic disorders in animals (i.e., they are antipsychotic agents), in view of their ability to act as dopamine-2 antagonists ($D_2$-antagonists). In addition, they also have the ability to reverse haldol-induced catalepsy in the rat. Hence, they are able to function as antipsychotic agents in animals, including humans, without causing any extra pyramidal side effects. Moreover, the neuroleptic activity of the compounds of the present invention is such that they are particularly useful for treating psychotic disorders in human subjects. For example, these compounds are useful in treating psychotic disorders of the schizophrenic types, and especially for removing or ameliorating such symptoms and conditions as anxiety, agitation, tension, excessive agression and social and/or emotional withdrawal, etc., that one normally encounters when dealing with psychotic patients.

The herein described N-substituted arylpiperidine compounds of this invention can be administered via either the oral or parenteral routes. In general, these compounds are most desirably administered in doses ranging from about 5.0 mg. up to about 500 mg. per day, although variations will necessarily occur depending upon the weight and condition of the subject being treated and the particular route of pharmaceutical administration chosen. However, a dosage level that is in the range of from about 0.07 mg. to about 7.0 mg. per kg. of body weight per day is most desirably employed. Nevertheless, variations may still occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing harmful side effects provided that such higher dose levels are first divided into several small doses for administration throughout the day.

The N-substituted arylpiperidine compounds of this invention may be administered alone or in combination with pharmaceutically acceptable carriers by either of the two routes previously indicated, and such administration can be carried out in single or multiple dosages. More particularly, the novel thereapeutic agents of the invention can be administered in a wide variety of different dosage forms, i.e., they may be combined with various pharmaceutically acceptable inert carriers in the form of tablets, capsules, lozenges, troches, hard candies, powders, sprays, suppositories, jellies, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium sterarate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of these N-substituted arylpiperidines in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled art.

The anti-psychotic activity of the compounds of the present invention as neuroleptic agents for the control of various psychotic disorders is determined primarily by a study of their ability to suppress $^3$[H]-N-propylnorapormorphine (dopamine-2 receptor) uptake in the brain of rate (in vitro). This study is carried out in a standard $^3$[H]-N-propylnorapomorphine binding assay test, where the amount of radioactivity is determined by liquid scintillation counting. In this way, the compounds can be rated in terms of their ability to reduce the amount of radioactivity caused by the aforesaid dopamine-2-receptor.

PREPARATION A

A 100 ml. three-necked round-bottomed reaction flask equipped with reflux condenser and addition funnel was flame-dried under a nitrogen atmosphere. To this flask, there were then added 35 ml. of anhydrous ether, two drops of 1,2-dibromoethane, 1.0 mg. of iodine and 1.2 g. (0.05 mole) of magnesium turnings. The ethereal mixture was then vigorously stirred, while 6.68 ml. (0.048 mole) of 1-bromonaphthalene were added thereto in a dropwise manner. Upon completion of this step, the resulting reaction mixture (already warm due to the exothermic nature of the reaction) was maintained with stirring at 39° C. for a period of 2.5 hours and then cooled to 5° C. with the aid of an ice bath. At this point, the resulting thick brown suspension was further stirred (at 5° C.), while a solution consisting of 6.49 ml. (0.030 mole) of 1-benzyl-4-piperidone (available from the Aldrich Chemical Company, Inc. of Milwaukee, Wisconsin) dissolved in 10 ml. of tetrahydrofuran was added thereto in a dropwise manner. After the addition was complete, the ice bath was removed and the final reaction mixture was stirred at room temperature (ca. 20° C.) for a period of three hours. The spent reaction mixture was next poured into a cooled saturated ammonium chloride solution, and the resulting aqueous suspension was subsequently extracted with ethyl acetate. The ethyl acetate extracts so obtained were then combined, dried over anhydrous sodium sulfate and subsequently evaporated under reduced pressure to afford a residual oil consisting of 15 g. of crude product. The latter material was then chromatographed on a column of 200 g. of fine mesh silica gel, using ethyl acetate/hexanes (1:1 by volume) as the eluant, to ultimately yield 7.21 g. (76%) of pure 1-benzyl-4-hydroxy-4-(1-naphthyl) piperidine in the form of a light brown oil. The pure product was characterized by means of nuclear magnetic resonance data: NMR (CDCl$_3$) $\delta$ 7.0–8.0 (m, 12H), 3.50 (s, 2H), 2.0–3.0 (m, 9H).

PREPARATION B

The procedure described in Preparation A was repeated except that 1-bromo-3-trifluoromethylbenzene was the starting material employed in place of 1-bromonaphthaline, using the same molar proportions as before. In this particular case, the corresponding final product obtained was 1-benzyl-4-hydroxy-4-(3-trifluoromethylphenyl)piperidine (yield, 90%). The pure product was characterized by means of nuclear magnetic resonance data: NMR (CDCl$_3$)$\delta$ 7.0–8.0 (m, 9H), 3.60 (s, 2H), 1.8–3.0 (m, 9H).

PREPARATION C

The procedure described in Preparation A was repeated except that 1-bromo-2-methoxybenzene (o-bromoanisole) was the starting material employed in place of 1-bromonaphthalene, using the same molar proportions as before. In this particular case, the corresponding final product obtained was 1-benzyl-4-hydroxy-4-(2-methoxyphenyl)piperidine (yield, 80%). The pure product was characterized by means of nuclear magnetic resonance data: NMR (CDCl$_3$) δ 6.8–7.6 (m, 9H), 3.85 (s, 3H), 3.58 (s, 2H), 1.8–2.0 (m, 9H).

PREPARATION D

The procedure described in Preparation A was repeated except that 1-benzyl-3-piperidone was the starting material employed in place of 1-benzyl-4-piperidone, using the same molar proportions as before. In this particular case, the corresponding final product obtained was 1-benzyl-3-hydroxy-3-(1-naphthyl)-piperidine (yield, 54%). The pure product was characterized by means of nuclear magnetic resonance data: NMR (CDCl$_3$) δ 8.80 (m, 1H), 7.80 (m, 2H), 7.20–7.60 (m, 9H), 4.40 (br s, 1H), 3.69 (dd, 2H), 3.25 (d, 1H), 3.00 (d, 1H), 1.8–2.6 (m, 6H).

PREPARATION E

The procedure described in Preparation A was repeated except that 1-bromo-2-methoxybenzene (o-bromoanisole) and 1-benzyl-3-piperidone were the respective starting materials employed, using the same molar proportions as before. In this particular case, the corresponding final product obtained was 1-benzyl-3-hydroxy-3-(2-methoxyphenyl)piperidine (yield, 73%). The pure product was characterized by means of nuclear magnetic resonance data: NMR (CDCl$_3$) δ 6.8–7.6 (m, 9H), 3.78 (s, 3H), 3.50 (s, 2H), 1.8–2.9 (m, 9H).

PREPARATION F

To a well-stirred solution consisting of 5.0 g. (0.0158 mole) of 1-benzyl-4-hydroxy-4-(1-naphthyl)-piperidine (the product of Preparation A) dissolved in 40 ml. of trifluoroacetic acid, there was added in a dropwise manner 5.1 ml. (0.032 mole) of triethylsilane. The reaction mixture was then stirred at 5°–10° C. for a period of one hour, while being kept under a nitrogen atmosphere. Upon completion of this step, the cooled mixture was poured onto ice, the pH of the water in the resulting aqueous mixture was adjusted to pH 9.0 with 1N aqueous sodium hydroxide and the basified aqueous mixture was subsequently extracted with ethyl acetate. The ethyl acetate extracts were then combined, washed with water and dried over anhydrous sodium sulfate. After removal of the drying agent by means of filtration and the solvent by means of evaporation under reduced pressure, there was finally obtained a residual yellow oil. This oil was then chromatographed on 75 g. of fine mesh silica gel, using chloroform as the eluant. The appropriate fractions were then combined and subsequently evaporated in vacuo to ultimately yield 4.2 g. (88%) of pure 1-benzyl-3,4-dehydro-4-(1-naphthyl)-piperidine in the form of a colorless oil. The pure product was characterized by means of nuclear magnetic resonance data: NMR (CDCl$_3$) δ 7.2–8.1 (m, 12H), 5.75 (br s, 1H), 3.75 (s, 2H), 3.25 (m, 2H), 2.80 (t, 2H), 2.58 (m, 2H).

PREPARATION G

The procedure described in Preparation F is repeated except that 1-benzyl-4-hydroxy-4-(3-trifluoromethyllphenyl)piperidine (the product of Preparation B) is the starting material employed in place of 1-benzyl-4-hydroxy-4-(1-naphthyl)piperidine, using the same molar proportions as before. In this particular case, the corresponding final product obtained is 1-benzyl-3,4-dehydro-4-(3-trifluoromethylphenyl)piperidine.

PREPARATION H

The procedure described in Preparation F was repeated except that 1-benzyl-4-hydroxy-3-(1-naphthyl)-piperidine (the product of Preparation D) was the starting material employed in place of 1-benzyl-4-hydroxy-4-(1-naphthyl)piperidine, using the same molar proportions as before. In this particular case, the corresponding final product obtained was 1-benzyl-3,4-dehydro-3-(1-naphthyl)piperdine (yield, 89%). The pure product was characterized by means of nuclear magnetic resonance data: NMR (CDCl$_3$) δ 8.05 (m, 1H), 7.6–7.8 (m, 2H), 7.1–7.5 (m, 9H), 5.8 (br s, 1H), 3.65 (s, 2H), 3.25 (d, 2H), 2.72 (t, 2H), 2.40 (m, 2H).

PREPARATION I

The procedure described in Preparation F was repeated except that 1-benzyl-4-hydroxy-4-(2-methoxyphenyl)piperidine, (the product of Preparation C) was the starting material employed in place of 1-benzyl-4-hydroxy-4-(1-naphthyl)piperidine, using the same molar proportions as before. In this particular case, the corresponding final product obtained was 1-benzyl-3,4-dehydro-4-(2-methoxyphenyl)piperidine (yield, 78%). The pure product was characterized by means of nuclear magnetic resonance data: NMR (CDCl$_3$)δ 6.8–7.8 (m, 9H), 5.75 (br s, 1H), 3.80 (s, 3H), 3.65 (s, 2H ), 3.15 (m, 2H), 2.60 (m, 4H).

PREPARATION J

The procedure described in Preparation F was repeated except that 1-benzyl-4-hydroxy-3-(2-methoxyphenyl)piperidine (the product of Preparation E) was the starting material employed in place of 1-benzyl-4-hydroxy-4-(1-naphthyl)piperidine, using the same molar proportions as before. In this particular case, the corresponding final product obtained was 1-benzyl-3,4-dehydro-3-(2-methoxyphenyl)piperidine (yield, 66%). The pure product was characterized by means of nuclear magnetic resonance data: NMR (CDCl$_3$) δ 6.6–7.4 (m, 9H), 5.75(br s, 1H), 3.62 (s, 3H), 3.58 (s, 2H), 3.20 (m, 2H), 2.0–2.6 (m, 4H).

PREPARATION K

To a solution consisting of 5.7 g. (0.018 mole) of 1-benzyl-3,4-dehydro-4-(1-naphthyl)piperidine (the product of Preparation F) dissolved in 80 ml. of ethanol, there were added 40 ml. of formic acid and 2 g. of 10% palladium-on-carbon catalyst. The resulting reaction mixture was then stirred under a nitrogen atmosphere at room temperature (ca 20° C.) for a period of eight days. The final mixture was then filtered, and the resulting filtrate added to an equal volume of water. The pH of the aqueous mixture was then adjusted to pH 9.0 with concentrated aqueous sodium hydroxide and next extracted with ethyl acetate. The ethyl acetate extracts were then combined, washed with water and dried over anhydrous sodium sulfate. After removal of the drying agent by means of filtration and the solvent by means of evaporation under reduced pressure, there was finally obtained a colorless residual oil. The latter material was then chromatographed on a flash column of fine mesh silica gel, using chloroform/methanol (10:1 by volume) as the eluant. In this way, there were ultimately obtained 3.2 g. (80%) of pure 4-(1-naphthyl)piperidine. The pure product was characterized by means of nuclear magnetic resonance data: NMR (CDCl₃) δ 7.2–8.35 (m, 7H), 2.6–3.8 (m, 5H), 2.55 (br s, 1H), 1.5–2.2 (m, 4H).

PREPARATION L

The procedure described in Preparation K is repeated except that 1-benzyl-3,4-dehydro-4-(3-trifluormethylphenyl)piperidine (the product of Preparation G) was the starting material employed in place of 1-benzyl-3,4-dehydro-4-(1-naphthyl)piperidine, using the same molar proportions as before. In this particular case, the corresponding final product obtained is 4-(3-trifluoromethylphenyl)piperidine.

PREPARATION M

The procedure described in Preparation K was repeated except that 1-benzyl-3,4-dehydro-3-(1-napthtyl)-piperidine (the product of Preparation G) was the starting material employed in place of 1-benzyl-3,4-dehydro-4-(1-napthtyl)piperidine, using the same molar proportions as before. In this particular case, the corresponding final product obtained was 3-(1-naphthyl)piperidine (yield, 40%). The pure product was characterized by means of nuclear magnetic resonance data: NMR (CDCl₃)δ 8.15 (d, 1H), 7.80 (d, 1H), 7.65 (d, 1H), 7.15–7.55 (m, 4H), 1.6–3.8 (m, 10H).

PREPARATION N

The procedure described in Preparation K was repeated except that 1-benzyl-3,4-dehydro-4-(2-methoxyphenyl)piperidine (the product of Preparation H) was the starting material employed in place of 1-benzyl-3,4-dehydro-4-(1-naphthyl)piperidine, using the same molar proportions as before. In this particular case, the corresponding final product obtained was 4-(2-methoxyphenyl)piperdine (yield, 18%). The pure product was characterized by means of nuclear magnetic resonance data: NMR (CDCl₃)δ 6.8–7 (m, 4H), 3.60 (s, 3H), 1.40–3.6 (m, 10H).

PREPARATION O

The procedure described in Preparation K was repeated except that 1-benzyl-3,4-dehydro-3-(2-methoxyphenyl)piperidine (the product of Preparation J) was the starting the material employed in place of 1-benzyl-3,4-dehydro-4-(1-naphthyl)piperidine, using the same molar proportions as before. In this particular case, the corresponding final product obtained was 3-(2-methoxyphenyl)piperidine (yield, 32%). The pure product was characterized by means of nuclear magnetic resonance data: NMR (CDCl₃) δ 7.0–7.6 (m, 4H), 4.05 (s, 3H), 1.6–3.8 (m, 10H).

PREPARATION P

To a 250 ml. round-bottomed reaction flask equipped with reflux condenser and nitrogen-inlet tube, there were added 30.7 g. (0.230 mole) of aluminum chloride, 150 ml. of carbon disulfide and 3.8 ml. (0.048 mole) of chloroacetyl chloride. Stirring was commenced and there were then added 5.0 g. (0.037 mole) of oxindole to the stirred mixture, with the addition being carried out in a portionwise manner over a 15-minute period. The reaction mixture was next stirred for a further period of ten minutes, followed by refluxing for a period of two hours. Upon completion of this step, the warm reaction mixture was cooled to ambient temperature (ca. 20° C.) and poured onto crushed ice followed by vigorous stirring of the resulting aqueous mixture. The beige precipitate which formed at this point was subsequently recovered by means of suction filtration, washed with water and air-dried to constant weight. In this way, there were ultimately obtained 7.67 g. (97%) of pure 5-chloroacetyloxindole. The pure product was characterized by means of nuclear magnetic resonance data: NMR (DMSO-d₆)δ 3.40 (s, 2H), 5.05 (s, 2H), 6.8–7.9 (m, 3H).

PREPARATION Q

To a 100 ml. round-bottomed reaction flask equipped with reflux condenser and nitrogen-inlet tube, there were placed 5.0 g (0.0239 mole) of 5-chloroacetyloxindole (the product of Preparation P) and 18.5 ml. of trifluoroacetic acid. Stirring was then commenced and to the stirred solution, there were then added 8.77 ml. (0.0549 mole) of triethylsilane with constant external cooling being maintained to prevent exotherm. The final reaction mixture was then stirred at room temperature (ca. 20° C.) for a period of 16 hours. Upon completion of this step, the spent mixture was poured into ice water, with stirring, and the resulting beige precipitate was subsequently recovered from the aqueous mixture by means of suction filtration, washed well with water and hexane, and thereafter air-dried to constant weight. In this manner, there were ultimately obtained 3.0 g. (64%) of pure 5-(2-chloroethyl)oxindole, m.p. 168°–170° C. The pure product was further characterized by means of mass spectrum analysis and nuclear magnetic resonance data: mass spectrum, m/e 195/197 (30/11, parent), 1 47 (18), 146 (100), 118 (48), 91 (13), 77 (11); NMR (DMSO-d₆) δ 3.00 (t, 2H), 3.48 (s, 2H), 3.82 (t, 2H), 6.7–7.2 (m, 3H).

PREPARATION R

In a 125 ml. round-bottomed reaction flask equipped with a Dean-Stark trap, reflux condensr and nitrogen-inlet tube, there were placed 5.35 g. (0.029 mole) of d-camphoric anhydride, 2.49 g. (0.028 mole) of 4-hydroxy-n-butylamine and 60 ml. of toluene. The resulting reaction mixture was then refluxed for a period of 20 hours, while water of condensation was separated therefrom. Upon completion of this step, the spent reaction mixture was cooled to room temperature (ca. 20° C.) and then concentrated in vacuo to an oil, which was thereafter dissolved in ethyl acetate. The latter solution was then washed with 5% aqueous hydrochloric acid, 5% aqueous sodium hydroxide and finally with brine, followed by drying over anhydrous sodium sulfate. After removal of the drying agent by means of filtration and the solvent by means of evaporation under reduced pressure, there were finally obtained 6.0 g. (85%) of pure 3-(4-hydroxy-n-butyl)-1,8,8-trimethyl-3-azabicyclo[3.2.1]-octane-2,4-dione in the form of a residual oil. The pure product was characterized by means of mass spectrum analysis and nuclear magnetic resonance data: mass spectrum (%), 254 (18), 253 (18, parent), 236 (23), 235 (37), 226 (17), 223 (47), 222 (23), 220 (21), 209 (13), 208 (14), 206 (29), 195 (33), 194 (100), 182 (76), 181 (22), 166 (24), 138 (31), 137 (31), 136 (15), 124 (17), 123 (18), 112 (35), 111 (15), 110 (28), 109 (86), 108 (10), 105 (912), 98 (27), 97 (12), 96 (34), 95 (55), 93 (11), 91 (14); NMR (CDCl₃)δ 0.87 (two s, 6H), 1.11 (s, 3H), 1.3–1.5 (m, 4H), 1.65–1.95 (m, 2H), 2.54 (s, 1H), 3.2–3.7 (m, 4H).

PREPARATION S

In a 250 ml. round-bottomed reaction flask equipped with a nitrogen-inlet tube, there were placed 5.35 g.

(0.0211 mole) of 3-(4-hydroxy-n-butyl)-1,8,8-trimethyl-3-azabicyclo[3.2.1]octane-2,4-dione (the product of Preparation R), 4.43 g. of 4-tosyl chloride, 5.84 g. (0.0422 mole) of potassium carbonate and 70 ml. of pyridine. The resulting reaction mixture was then stirred initially at 0° C. and finally at room temperature (ca. 20° C. ) for a period of five hours. Upon completion of this step, the spent reaction mixture was poured into water and the resulting aqueous solution subsequently extracted with methylene chloride. The latter organic extract was next washed successively with water, cupric sulfate solution, sodium carbonate solution, water again and then brine, followed by drying over anhydrous sodium sulfate. After removal of the drying agent by means of filtration and the solvent by means of evaporation under reduced pressure, there were finally obtained 5.3 g. (62%) of pure 3-(4-tosyloxy-n-butyl)-1,8,8-trimethyl-3-azabicyclo[3.2.1]octane2,4-dione in the form of a residual oil. The pure product was characterized by means of mass spectrum analysis and nuclear magnetic resonance data: mass spectrum (%), 409 (10), 408 (31), 407 (11,parent), 252 (21), 237 (924), 236 (100), 235 (88), 226 (10), 220 (20), 207 (44), 206 (81), 194 (40), 182 (12), 173 (10), 166 (14), 155 (20), 138 (11), 137 (14), 136 (11), 112 (11), 110 (13), 109 (49), 108 (12), 107 (11), 96 (14), 95 (37), 93 (12), 91 (81); NMR (CDCl$_3$)$\delta$ 0.87 (two s, 6H), 1.11 (s, 3H), 3.5–3.7 (m, 2H), 3.9–4.1 (m, 2H), 7.2–7.8 (m, 4H).

EXAMPLE 1

A mixture consisting of 180 mg. (0.00018 mole) of 4-(1-naphthyl)piperidine (the product of Preparation K) 190 mg. (0.00085 mole) of 3-(2-chloroethyl)-2-methyl-4H-pyrido[1,2-a]pyrimidine-4-one (prepared as described in Published European Patent Application No. 196,132), 220 mg. (0.0022 mole) of sodium carbonate and 100 mg. of sodium iodide all dispersed in 20 ml. of methyl isobutyl ketone was refluxed for a period of 30 hours. The resulting reaction mixture was then cooled to room temperature (ca. 20° C.) and added to an equal volume of water (with stirring). The aqueous solution so obtained was next extracted with ethyl acetate, and the organic extracts were subsequently combined, dried over anhydrous sodium sulfate and filtered. After removal of the drying agent by means of filtration and the solvent by means of evaporation under reduced pressure, there was finally obtained a brown residual oil as the crude product. The latter material was then chromatographed on silica gel, using ethyl acetate/methanol (10:1 by volume) as the eluant, to ultimately afford 280 mg. (83%) of the pure N-substituted piperidine base derivative, viz., 3-{2-[4-(1-naphthyl)piperdinyl]ethyl}-2-methyl-4H-pyrido[1,2-a]pyrimidine-4-one. The pure base product was characterized by means of mass spectrum analysis and nuclear magnetic resonance data: mass spectrum, m/e 397.1 (parent peak); NMR (CDCl$_3$)$\delta$ 8.90 (d, 1H), 7–8.10 (m, 10H), 2.55 (s, 3H), 1.8–3.2 (m, 13H).

Treatment of the above base final product in 5.0 ml. of ethyl acetate with one equivalent of HCl in ethyl acetate (which was added dropwise) then gave a white precipitate, which was subsequently collected by means of suction filtration to yield 280 mg. of the hydrochloride salt.

EXAMPLE 2

The procedure described in Example 1 was repeated except that 4-[4-(2-chloroethyl)phenyl]-2-aminothiazole (first reported as the hydrobromide in Published European Patent Application No. 279,598) was the reactant employed in place of 3-(2-chloroethyl)-2-methyl-4H-pyrido[1,2-a]pyrimidine-4-one, using the same molar proportions as before. In this particular case, the corresponding final product obtained was 4-{{4-{2-[4-(1-naphthyl)piperidinyl]ethyl}phenyl}}thiazole-2-amine (yield, 59%), which was also converted to the hydrochloride salt. The pure base product was characterized by means of mass spectrum analysis and nuclear magnetic resonance data: mass spectrum, m/e 413.2 (parent peak); NMR (CDCl$_3$)$\delta$ 8.12 (d, 1H), 7.85 (d, 1H), 7.7–7.8 (m, 3H) 7.2–7.35, 7.4–7.6 (m, 3H), 6.67 (s, 1H), 5.28 (s,2H), 3.35 (m,1H), 3.05 (d,2H), 2.90 (m, 2H), 2.72 (m, 2H), 2.35 (m, 2H), 1.9–2.2 (m, 4H).

EXAMPLE 3

The procedure described in Example 1 was repeated except that 8-(4-chloro-n-butyl)-8-azaspiro[4.5]decane-7,9 dione (prepared as described in U.S. Pat. No. 3,717,634) was the reactant employed in place of 3-(2-chloroethyl)-2-methyl-4H-pyrido-[1,2-a]pyrimidine-4-one, using the same molar proportions as before. In this particular case, the corresponding final product obtained was 8-{4-[4-(1-naphthyl)-1-piperidinyl]butyl}-8-azaspiro[4.5]decane-7,9-dione (yield, 33%) which was also converted to the hydrochloride salt. The pure base product was characterized by means of mass spectrum analysis and nuclear magnetic resonance data: mass spectrum, m/e 432.3 (parent peak); NMR (CDCl$_3$)$\delta$ 8.07 (d, 1H), 7.85 (d, 1H), 7.68 (d, 1H), 7.3–7.5 (m, 4H), 2.58 (s, 4H), 1.4–3.8 (m, 25H).

EXAMPLE 4

The procedure described in Example 1 was repeated except that 5-(2-chloroethyl)oxindole (the product of Preparation Q) was the reactant employed in place of 3-(2-chloroethyl)-2-methyl-4H-pyrido-[1,2-a]pyrimidine-4-one, using the same molar proportions as before. In this particular case, the corresponding final product obtained was 5-{2-[4-(1-naphthyl)-1-piperidinyl]ethyl}oxindole (yield, 39%), which was also converted to the hydrochloride salt. The pure base product was characterized by means of mass spectrum analysis and nuclear magnetic resonance data: mass spectrum, m/e 369.2 (parent peak); NMR (CDCl$_3$)$\delta$ 8.90 (br s, 1H), 8.15 (d, 1H, 7.85 (d, 1H), 7.70 (d, 1H), 7.35–7.55 (m, 4H), 7.08 (s, 1H), 7.05 (d, 1H), 6.78 (d, 1H), 3.55 (s, 2H), 1.9–3.4 (m, 12H).

EXAMPLE 5

The procedure described in Example 1 was repeated except that 3-(1-naphthyl)piperidine (the product of Preparation M) and 5-(2-chloroethy)oxindole (the product of Preparation Q) were the respective starting materials employed, using the same molar proportions as before. In the particular case, the corresponding final product obtained was 5-{2-[3-(1-naphthyl)-1-piperidinyl]ethyl}oxindole (yield, 43%), which was also converted to the hydrochloride salt. The pure base product was characterized by means of mass spectrum analysis and nuclear magnetic resonance data: mass spectrum, m/e 371.1; NMR (CDCl$_3$)$\delta$ 8.25 (br s, 1H), 8.15 (d, 1H), 7.82 (d, 1H), 7.68 (d, 1H), 7.3–7.5(m, 4H), 7.04 (s,1H ), 6.95 (d,1H), 6.70 (d,1H), 3.70 (m,1H), 3.45 (s, 2H), 3.25 (d, 1H), 3.15 (d, 1H), 1.80–2.80 (m, 10H).

EXAMPLE 6

The procedure described in Example 1 was repeated except that 3-(4-tosyloxy-n-butyl)-1,8,8-trimethyl-3-azabiocyclo[3.2.1]-octane-2,4-dione (the product of Preparation S) was the reactant employed in place of 3-(2-chloroethyl)-2-methyl-4H-pyrido[1,2-a]pyrimidine-4-one, using the same molar proportions as before. In this particular case, the corresponding final product obtained was 3-{4-[4-(1-naphthyl)-1-piperidinyl]-n-butyl}-1,8,8-trimethyl-3-azabicyclo[3.2.1]octane-2,4-dione (yield, 70%), which was also converted to the hydrochloride salt. The pure base product was characterized by means of mass spectrum analysis and nuclear magnetic resonance data: mass spectrum, m/e 446.1 (parent peak); NMR (CDCl$_3$)$\delta$ 8.05 (d, 1H), 7.80 (d, 1H), 7.68 7.3–7.52 (m, 4H), 1.15 (s, 3H), 0.95 (s, 3H), 0.93 (s, 3H), 1,2–3.8 (m, 22H).

EXAMPLE 7

The procedure described in Example 1 was repeated except that 3-(1-naphthyl)piperidine (the product of Preparation M) and 3-(4-tosyloxy-n-butyl)-1,8,8-trimethyl-3-azabicyclo[3.2.1]-octane-2,4-dione (the product of Preparation S) were the respective starting materials employed, using the same molar proportions as before. In this particular case, the corresponding final product obtained was 3-{4-[3-(1-naphthyl)1-piperidinyl]-n-butyl}-1,8,8-trimethyl-3-azabicyclo-[3.2.1]octane-2,4-dione (yield, 20%), which was also converted to the hydrochloride salt. The pure base product was characterized by means of mass spectrum analysis and nuclear magnetic resonance data: mass spectrum, m/e 446.2 (parent peak); NMR (CDCl$_3$)$\delta$ 8.15 (d, 1H), 7.75 (d, 1H), 7.65 (d, 1H), 7.30–7.55 (m, 4H), 1.15 (s, 3H), 0.95 (s, 6H), 1.2–3.7 (m, 22H).

EXAMPLE 8

The procedure described in Example 1 was repeated except that 4-phenylpiperidine (available from the Aldrich Chemical Company, Inc. of Milwaukee, Wis.) and 2-(p-hydroxyphenyl)ethyl chloride were the respective starting materials employed, using the same molar proportions as before. In this particular case, the corresponding final product obtained was 4-[2-(4-phenyl-1-piperidinyl)ethyl]phenol (yield, 22%), which was also converted to the hydrochloride salt.

Anal. Calcd. for C$_{19}$H$_{23}$.NO HCl: C, 71.79; H, 7.61; N, 4.41. Found: C, 71.63; H, 7.42; N, 4.13.

EXAMPLE 9

The procedure described in Example 1 was repeated except that 4-(3-trifluoromethylphenyl)piperidine (the product of Preparation L) and 2-(p-hydroxyphenyl)ethyl chloride were the respective starting materials employed, using the same molar proportions as before. In this particular case, the corresponding final product obtained was 4-{2-[4-(3-trifluoromethylphenyl)-piperidinyl]ethyl}-phenol-(yield, 65%), which was also converted to the hydrochloride salt. The pure base product was characterized by means of nuclear magnetic resonance data: NMR (CDCl$_3$)$\delta$ 6.8–7.6 (m, 8H), 0.6–4.0 (m, 14H). The hydrochloride salt melted at 207°–210° C. and was further characterized by means of elemental analysis.

Anal. Calcd. for C$_{20}$H$_{22}$F$_3$NO.HCl: C, 62.25; H, 6.01; N, 3.63. Found: C, 62.01; H, 5.92; N, 3.58.

EXAMPLE 10

The procedure described in Example 1 was repeated except that 4-(3-trifluoromethylphenyl)piperidine (the product of Preparation L) and 2-phenoxyethyl chloride were the respective starting materials employed, using the same molar proportions as before. In this particular case, the corresponding final product obtained was 1-{2-[4-(3-trifluoromethylphenyl)-1-piperidinyl]ethyloxy}benzene (yield, 28%), which was also converted to the hydrochloride salt. The pure base product was characterized by means of mass spectrum analysis and nuclear magnetic resonance data: mass spectrum, m/e 349 (parent peak); NMR (CDCl$_3$)$\delta$ 6.8–7.6 (m, 9H), 3.8–4.3 (m, 3H), 1.6–3.4 (m, 10H).

EXAMPLE 11

The procedure described in Example 1 was repeated except that 4-(2-methoxyphenyl)piperidine (the product of Preparation N) and 4-[4-(2-chloroethyl)phenyl]-2-aminothiazole (first reported as the hydrobromide in Published European Patent Application No. 279,598) were the respective starting materials employed, using the same molar proportions as before. In this particular case, the corresponding final product obtained was 4-{{4-{2-[4-(2-methoxyphenyl)-1-piperidinyl]ethyl} phenyl}}-thiazole-2-amine (yield, 22%), which was also converted to the hydrochloride salt. The pure base product was characterized by means of mass spectrum analysis and nuclear magnetic resonance data: mass spectrum, m/e 392.2 (parent peak); NMR (CDCl$_3$)$\delta$ 7.65 (d, 1H), 6.8–7.3 (m, 7H), 6.65 (s, 1H), 5.16 (d, 2H), 3.80 (s, 3H), 1.7–3.2 (m, 13H).

EXAMPLE 12

The procedure described in Example 1 was repeated except that 3-(2-methoxyphenyl)piperidine (the product of Preparation of O) and 4-[4-(2-chloroethyl)phenyl]-2-aminothiazole (first reported as the hydrobromide in Published European Patent Application No. 279,598) were the respective starting materials employed, using the same molar proportion as before. In this particular case, the corresponding final product obtained was 4-{{4-55 2-[3-(2-methoxyphenyl)-1-piperidinyl]ethyl} phenyl}}-thiazole-2-amine (yield, 31%), which was also converted to the hydrochloride salt. The pure base product was characterized by means of mass spectrum analysis and nuclear magnetic resonance data: mass spectrum, m/e 392.9 (parent peak); NMR (CDCl$_3$)$\delta$ 6.60 (d, 1H), 7.1–7.2 (m, 5H), 6.8–6.9 (m, 2H), 6.80 (s, 1H), 5.0 (s, 2H), 3.76 (s, 3H), 1.6–3.6 (m, 13H).

EXAMPLE 13

The procedure described in Example 1 was repeated except that 3-(2-methoxyphenyl)piperidine (the product of Preparation O) and 4-(4-chloro-n-butyl)phenyl-2-aminothiazole (first reported as the hydrobromide in Published European Patent Application No. 279,598) were the respective starting materials employed, using the same molar proportions as before. In this particular case, the corresponding final product obtained was 4-{{4-{4-[3-(2-methoxyphenyl)-1-piperidinyl]n-butyl} phenyl}}-thiazole-2-amine (yield, 45%), which was also converted to the hydrochloride salt. The pure base product was characterized by means of mass spectrum analysis and nuclear magnetic resonance data: mass spectrum, m/e 421.1 (parent peak); NMR (CDCl$_3$)$\delta$ 6.80 (d, 1H), 7.05–7.2 (m, 5H, 6.85 (m, 2H), 6.60 (s, 1H), 4.92 (s, 2H), 3.75 (s, 3H), 1.4–3.4 (m, 17H).

EXAMPLE 14

The procedure described in Example 1 was repeated except that 4-(2-methoxyphenyl)piperidine (the product of Preparation N) and 4-[4-(4-chloro-n-butyl)phenyl]-2-aminothiazole (first reported as the hydrobromide in Published European Patent Application No. 279,598) were the respective starting materials employed, using the same molar proportions as before. In this particular case, the corresponding final product obtained was 4-{{4-{4-[4-(2-methoxyphenyl)-1-piperidinyl]-n-butyl}phenyl}}thiazole-2amine (yield, 44%), which was also converted to the hydrochloride salt. The pure base product was characterized by means of mass spectrum analysis and nuclear magnetic resonance data: mass spectrum, m/e 421.3 (parent peak); NMR (CDCl$_3$)$\delta$ 7.75 (d, 1H), 7.25 (m, 2H), 6.90 (m, 4H), 6.85 (s, 1H), 5.0 (br, s, 2H), 3.85 (s, 3H), 1.8–3.6 (m, 17H).

EXAMPLE 15

The procedure described in Example 1 was repeated except that 3-(2-methoxyphenyl)piperidine (the product of Preparation O) and 8-4-(4-chloro-n-butyl)-8-azaspiro[4.5]decane-7,9-dione-(prepared as described in U.S. Pat. No. 3,717,634) were the respective starting materials employed, using the same molar proportions as before. In this particular case, the corresponding final product obtained was 8-{4-[3-(2-methoxyphenyl)-1-piperidinyl]-n-butyl}-8-azaspiro[4.5]decane-7,9-dione (yield, 32%), which was also converted to the hydrochloride salt. The pure base product was characterized by means of mass spectrum analysis and nuclear magnetic resonance data: mass spectrum, m/e 412.3 (parent peak); NMR (CDCl$_3$) $\delta$ 7.15 (m, 2H), 6.85 (m, 4H), 3.81 (s, 1H), 2.58 (s, 4H), 1.6–3.8 (m, 25H).

EXAMPLE 16

The procedure described in Example 1 was repeated except that 4-(2-methoxyphenyl)piperidine (the product of Preparation N) and 5-(2-chloroethyl)oxindole (the product of Preparation Q) were the respective starting material employed, using the same molar proportions as before. In this particular case, the corresponding final product obtained was 5-{2-[4-(2-methoxyphenyl)-1-piperidinyl]ethyl}oxindole (yield, 55%), which was also converted to the hydrochloride salt. The pure base product was characterized by means of mass spectrum analysis and nuclear magnetic resonance data: mass spectrum, m/e 351.1 (parent peak); NMR (CDCl$_3$) $\delta$ 6.75–7.25 (m, 7H), 3.81 (s, 3H), 3.50 (s, 2H), 1.8–3.2 (m, 14H).

EXAMPLE 17

The procedure described in Example 1 was repeated except that 4-(2-methoxyphenyl)piperidine (the product of Preparation N) and 3-(4-tosyloxy-n-butyl)-1,8,8-trimethyl-3-azabicyclo-[3.2.1]octane-2,4-dione (the product of Preparation S) were the respective starting materials employed, using the same molar proportions as before. In this particular case, the corresponding final product obtained was 3-{4-[4-(2-methoxyphenyl)-1-piperidinyl]-n-butyl}-1,8,8-trimethyl-3-azabicyclo[3.2.1]-octane-2,4-dione (yield, 92%), which was also converted to the hydrochloride salt. The pure base product was characterized by means of mass spectrum analysis and nuclear magnetic resonance data: mass spectrum, m/e 426.2 (parent peak); NMR (CDCl$_3$) $\delta$ 7.25 (m, 2H), 6.95 (m, 2H), 3.85 (s, 3H), 3.72 (m, 1H), 1.7–3.2 (m, 21H), 1.24 (s, 3H), 1.01 (s, 6H).

EXAMPLE 18

The procedure described in Example 1 was repeated except that 3-(2-methoxyphenyl)piperidine (the product of Preparation O) and 3-(4-tosyloxy-n-butyl)-1,8,8-trimethyl-3-azabicyclo-[3.2.1]octane-2,4-dione (the product of Preparation S) were the respective starting materials employed, using the same molar proportions as before. In this particular case, the corresponding final product obtained was 3-{4-[3-(2-methoxyphenyl)-1-piperidinyl]-n-butyl}-1,8,8-trimethyl-3-azabicyclo[3.2.1]-octane-2,4-dione (yield, 38%), which was also converted to the hydrochloride salt. The pure base product was characterized by means of mass spectrum analysis and nuclear magnetic resonance data: mass spectrum, m/e 426.4 (parent peak); NMR (CDCl$_3$) $\delta$ 7.12 (m, 2H), 6.58 (m, 2H), 3.78 (s, 3H), 1.15 (s, 3H), 0.95 (s, 6H), 1.3–3.7 (m, 22H).

EXAMPLE 19

The N-substituted arylpiperidine compounds of Examples 1–18, respectively, were tested for antipsychotic activity in rats, using the standard $^3$[H]-N-propylnorapomorphine binding assay test, according to the general procedure described by K. Fuxe et al., as reported in the *European Journal of Pharmacology*, vol. 100, p. 127 (1984).

In this procedure, the brain was quickly removed from a decapitated rat and the caudate and mesolimbic areas were substantially dissected therefrom to afford an average of ca. 150–180 mg. of material per rat. The caudate and mesolimbic areas were then homogenized on admixture with 40 volumes of ice-cold 15 mM Tris (i.e., tromethamine which is 2-amino-2-hydroxymethyl-1,3-propanediol) hydrochloride buffer having a pH of 7.5, which also contained 1.0 mM ethylenediaminetetraacetic acid (EDTA) and 0.01% ascorbic acid. The homogenate was next centrifuged at 35,000×G for a period of ten minutes. The supernatant liquid was then decanted, and the resulting pellet subsequently resuspended in 40 volumes of fresh, ice-cold Tris-EDTA buffer and homogenized, followed by incubation 37° C. for a period of ten minutes. The resulting homogenate was next re-centrifuged at 35,000×G for another ten-minute period, followed by decantation of the supernatant liquid. The pellet obtained in this manner was then resuspended again in the Tris-EDTA buffer, followed by a repeat of the centrifugation and decantation steps, with the final pellet being resuspended once more in 15 mM Tris-EDTA buffer at a concentration level of 11.25 mg./ml. This completed the production of the tissue preparation phase of the overall procedure.

The radioligand binding procedure was then carried out in the following manner, viz., by initiating the incubation reaction by first adding the tissue preparation to duplicate sets of tubes, with each tube ultimately containing 800 82 L. of tissue suspension (final concentration, 9.0 mg./ml.), 100 $\mu$L. of $^3$[H]-N-norapomorphine as the radioactive ligand made up to a final concentration of 0.32 nM and 100 $\mu$L. of the test compound or buffer (at ten times the final concentration). The final reaction mixture was next vortexed and incubated at 25° C. for a period of 30 minutes (using a 25° C. water bath for these purposes). Nonspecific binding was defined throughout the test by means of 2.0 $\mu$M of (+)-butaclamol, a highly potent neuroleptic agent. Upon completion of the reaction step, the incubation period was terminated by subjecting the tubes to rapid filtration under vacuum through fiber filters, followed by two rinses with 5 ml. of ice-cold 15 mM Tris-EDTA buffer for each tube. The filters thus obtained were next soaked in 10 ml. of Aquasol 2 (a registered trademark name of New England Nuclear Corporation of Boston, Mass. for a liquid scintillation counter material), vortexed and then allowed to stand overnight (ca. 18 hours) at ambient temperatures in order to extract radioactivity. The amount of radioactivity was determined by liquid scintillation counting, using a Beta counter at 53% counting efficiency. The $IC_{50}$ values were thereafter calculated by using standard statistical methods. On this basis, the ability of each test compound to reduce the amount of radioactivity caused by $^3[H]$-N-propylnorapomorphine is given as an $IC_{50}$ value, expressed in terms of nM units.

In this way, the N-substituted arylpiperidine compounds of formula I that were reported as final products in Examples 1–18, respectively, were all assayed and found to be capable of inhibiting $^3[H]$-N-propylnorapomorphine binding at its dopamine-2 receptor site at the previously-indicated dose level tested. The results obtained in this manner are shown below in the following table, where the binding assay for each compound is reported in terms of the previously-discussed $IC_{50}$ value:

| Compound | $IC_{50}$ (nM) |
| --- | --- |
| Product of Example 1 | 113.9 |
| Product of Example 2 | 196.4 |
| Product of Example 3 | 238.6 |
| Product of Example 4 | 184.0 |
| Product of Example 5 | 168.6 |
| Product of Example 6 | 169.0 |
| Product of Example 7 | 1109.5 |
| Product of Example 8 | 362.0 |
| Product of Example 9 | 601.0 |
| Product of Example 10 | 210.0 |
| Product of Example 11 | 36.3 |
| Product of Example 12 | 149.8 |
| Product of Example 13 | 246.5 |
| Product of Example 14 | 51.6 |
| Product of Example 15 | 531.3 |
| Product of Example 16 | 52.2 |
| Product of Example 17 | 51.5 |
| Product of Example 18 | 678.7 |

I claim:

1. An N-substituted arylpiperidine compound of the formula:

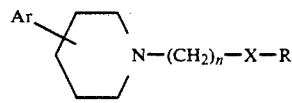

or a pharmaceutically acceptable acid addition salt thereof, wherein

Ar is phenyl, fluorophenyl, chlorophenyl, trifluoromethylphenyl, methoxyphenyl, tolyl, or naphthyl optionally substituted with fluorine, chlorine, trifluoromethyl or methoxy;

n is an integer of from two to four, inclusive;

X is oxygen, sulfur or a direct link; and

R is 2-amino-4-thiazoylphenyl.

2. A compound as claimed in claim 1 wherein Ar is attached to the 3-position of the piperidine ring.

3. A compound as claimed in claim 1 wherein Ar is attached to the 4-position of the piperidine ring.

4. A compound as claimed in claim 1 wherein Ar is methoxyphenyl or naphthyl and X is a direct link.

5. A compound as claimed in claim 1 wherein Ar is 2-methoxyphenyl, n is two or four and R is 4-(2-amino-4-thiazolyl)phenyl.

6. A compound as claimed in claim 3 wherein Ar is phenyl, trifluoromethylphenyl, methoxyphenyl or naphthyl, and X is oxygen or a direct link.

7. A compound as claimed in claim 6 wherein X is a direct link.

8. A compound as claimed in claim 7 wherein Ar is 2-methoxyphenyl, n is two or four and R is 4-(2-amino-4-thiazolyl)phenyl.

9. A compound as claimed in claim 7 wherein Ar is 1-naphthyl, n is two and R is 4-(2-amino-4-thiazolyl)phenyl.

10. 4-{{4-{2-[4-(2-Methoxyphenyl)-1-piperidinyl]ethyl}phenyl}}thiazole-2-amine.

11. 4-{{4-{4-[4-(2-Methoxyphenyl)-1-piperidinyl]-n-butyl}phenyl}}thiazole-2-amine.

12. An anti-psychotic pharmaceutical composition suitable for oral or parenteral administration comprising a pharmaceutically acceptable carrier or diluent and a compound as claimed in claim 1 in an amount effective for removing or ameliorating the symptoms of psychotic schizophrenia.

13. A method for removing or ameliorating the symptoms of psychotic schizophrenia in an afflicted mammal in need of such treatment, which comprises administering to said subject an effective anti-psychotic amount of a compound as claimed in claim 1.

14. The method as claimed in claim 13 wherein said mammal is a human subject.

* * * * *